(12) United States Patent
Hall et al.

(10) Patent No.: US 7,256,879 B2
(45) Date of Patent: *Aug. 14, 2007

(54) SEMICONDUCTOR ARRAY TESTER

(75) Inventors: Benjamin L. Hall, Corning, NY (US); Martin Hu, Painted Post, NY (US); Mike J. White, Lawrenceville, PA (US); Chung-En Zah, Holmdel, NJ (US)

(73) Assignee: Corning Incorporated, Corning, NY (US)

( * ) Notice: Subject to any disclaimer, the term of this patent is extended or adjusted under 35 U.S.C. 154(b) by 560 days.

This patent is subject to a terminal disclaimer.

(21) Appl. No.: 10/733,903

(22) Filed: Dec. 11, 2003

(65) Prior Publication Data

US 2005/0128469 A1 Jun. 16, 2005

(51) Int. Cl.
*G01R 1/04* (2006.01)
*G01R 31/26* (2006.01)

(52) U.S. Cl. .................. 356/121; 324/158.4; 324/765; 356/237.1

(58) Field of Classification Search ................ 356/121, 356/237.1; 324/158.1, 754, 765, 767
See application file for complete search history.

(56) References Cited

U.S. PATENT DOCUMENTS

| | | | |
|---|---|---|---|
| 5,703,892 A | 12/1997 | Claisse et al. ................. | 372/32 |
| 5,767,507 A | 6/1998 | Unlu et al. ................... | 250/225 |
| 5,949,534 A * | 9/1999 | Guttman et al. ............. | 356/121 |
| 6,175,446 B1 | 1/2001 | Alphonse ..................... | 359/344 |
| 6,330,378 B1 | 12/2001 | Forrest et al. ................. | 385/14 |
| 6,483,580 B1 | 11/2002 | Xu et al. ..................... | 356/300 |
| 6,501,260 B1 * | 12/2002 | Hu et al. ................. | 324/158.1 |
| 2002/0114067 A1 | 8/2002 | Walter et al. ................ | 359/344 |
| 2003/0095264 A1 | 5/2003 | Ruchet ....................... | 356/491 |

FOREIGN PATENT DOCUMENTS

| | | |
|---|---|---|
| EP | 1220394 A2 | 7/2002 |
| JP | 02-240990 | 9/1990 |
| WO | WO 01/36931 | 5/2001 |

OTHER PUBLICATIONS

"Theory of Spontaneous Emission Noise in Open Resonators and its Applications to Lasers and Optical Amplifiers" C. H. Henry J. of Lightwave Technology, vol. Lt-4, No. 3, Mar. 1986.
"A Comparison of Far-Field Methods for Determining Mode Field Diameter of Single-Mode Fibers Using Both Gaussian and Petermann Definitions" T. J. Drapela, et al J. of Lightwave Technology, vol. 7, No. 8, Aug. 1989.

* cited by examiner

*Primary Examiner*—Richard A. Rosenberger
(74) *Attorney, Agent, or Firm*—Juliana Agon; Tina N. Thompson

(57) ABSTRACT

An array tester (10) characterizes individual ones (111) of a semiconductor devices of an array (11) based on polarization-resolving an optical far-field measurement of the individual chips (111) as a function of angular position. Two pairs of TM and TE detectors (41*a-b* and 42*a-b*) or one pair displaceable by ninety degrees, move in vertical and horizontal arc paths or fixed around a fixed position of a selected device of an array to sample the far-fields.

20 Claims, 7 Drawing Sheets

SEMICONDUCTOR ARRAY TESTER

BACKGROUND OF THE INVENTION

1. Field of the Invention

The present invention relates generally to testing of semiconductors or other eletro-optical devices, and particularly to testing of bars, stacks or other arrays which are intermediate structures in the manufacture of chips.

2. Technical Background

Electro-optical devices, such as semiconductor lasers, have become important commercial components. They are used in a wide variety of applications ranging from the readout sources, using lasers, in compact disks to the transmitters in optical fiber communication systems. A semiconductor optical amplifier (SOA) is basically a laser without the mirrors to form the laser cavity. SOAs also have wide applications in optical communications, such as in amplification, arrays for ultra-fast switching, interconnection, wavelength conversion, and 2R-3R regeneration. The laser, SOA, and other components, such as modulators can be combined to form an intergrated device, such as a transmitter, transceiver, switch, regenerator, or integrated modulator chip.

While new applications in high-speed telecommunication networks continue to emerge, how to ensure that chips are reliable and manufacturable is the most challenging issue. One proven approach to this issue is to deploy tight quality control by using testing systems that characterize the device in many aspects.

Chips are manufactured on wafers or substrates which are processed and further divided into sections or quarters. The sections are further divided into bars or other arrays by breaking or cleaving the sections along the scribe lines. For use as a laser, the sections are cleaved to form facets along the elongated sides of the sections. The laser bar or array contain many laser diodes. Similarly, SOA chips are formed from the semiconductor section breaking along the scribe lines. To prevent the facets from acting as reflective mirrors, both of the cleaved facets of a SOAs are either coated with anti-reflection (AR) films or the facets are cleaved at an angle with respect to the SOA stripe. One SOA bar or section contains multiple SOAs, in quantity of 1 to 100 or more per each bar.

During the process of array or bar fabrication from the wafer to the final packaging of individual chips, the first stage where these chips exhibit both electrical and optical characteristics is when the bars or arrays are formed. Therefore, it is desired to characterize or otherwise screen for passing at this early stage by probing and testing all the chips, in a batch process, when they are still in the form of a bar or array. The chips or other devices that do not meet specifications will be scrapped before entering into further labor-costing or time-costing stages, i.e. packaging and life-testing or burn-in.

Usually, a full procedure of laser bar testing includes six measurements for each laser that is being probed: front-facet light versus current, back-facet light versus current, voltage versus current, horizontal far field pattern, vertical far field pattern and an optical spectrum analysis. A system that performs one or all of these measurement functions is called a laser bar tester.

The traditional practice of testing SOA involves using two optical fibers, one as input and the other as output. Light is injected into the SOA by the input fiber and the output light is collected from the SOA by the output fiber. The fiber-to-fiber parameters, e.g. optical gain, polarization dependent gain (PDG), gain tilt, and noise figure are measured. Therefore testing of SOA has been limited to fully- or partially-packaged devices, where the input fiber and output fiber are either permanently pigtailed or must be brought into precise proximity with the SOA. For the pigtailed case, a bad device means tremendous waste of material and labor hours per device; for the proximity case, the measurement throughput is low because aligning fibers to an SOA is very time consuming. The traditional fiber-fiber system is also costly to build and hard to maintain. A measurement system of high throughput that is capable of screening SOAs in the early fabrication stage is thus indispensable in order to reduce the cost, improve yield and provide quick feedback to design changes.

Therefore, there is a need to improve the semiconductor bar or array tester to minimize damage to the chips due to the testing process while maximizing efficiency.

SUMMARY OF THE INVENTION

One aspect of the present invention is a tester for characterizing individual ones of a semiconductor devices of an array based on polarization-resolving and wavlength-resolving an optical far-field measurement of the individual chips as a function of angular position.

In another aspect, the present invention includes at least two pairs of TM and TE detectors or one pair of detectors that can be displaced for TM or TE measurements, each TM and TE pair moving in vertical and horizontal arc paths or fixed around a fixed position of a selected device of an array to sample the far-fields.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF THE PREFERRED EMBODIMENTS

Figure 1:
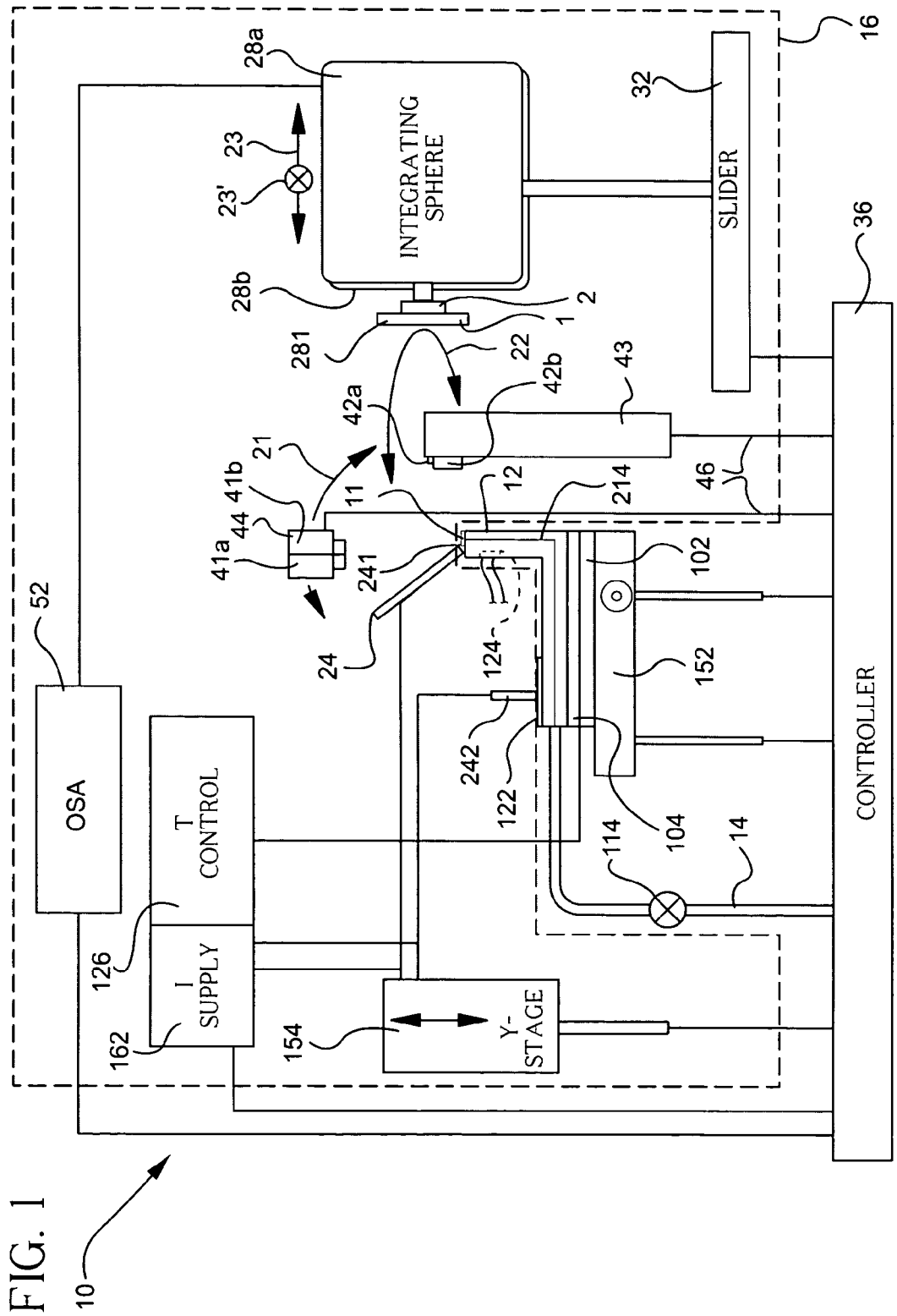
FIG. 1 is a schematic view of an array tester, in accordance with the present invention.

Reference will now be made in detail to the present preferred embodiment of the invention, an example of which is illustrated in the accompanying drawings. Wherever possible, the same reference numbers will be used throughout the drawings to refer to the same or like parts. However, not all similar parts are labeled for simplifying the drawings. Exemplary embodiment of the array tester of the present invention is shown in FIG. 1, and is designated generally throughout by reference numeral 10.

In accordance with the invention, the present invention for a tester and method for characterizing individual ones of a semiconductor devices of an array 11 includes a holder 12 for securing the array in a fixed position. The advantages of a fixed array or bar mounting are the ease of handling and the minimization of testing errors due to the movement of the array 11. Eventhough only one example is shown, other movable or non-movable detector systems surrounding a fixed laser array can be implemented, in accordance with the teachings of the present invention.

As embodied herein as one example out of other various fixed holder arrangements, and depicted in FIG. 1, the holder 12 includes a selective application of vacuum suction 14 applied to the array 11 abutted against a suitable fixture, such as a vacuum chuck, for releasing or securing the array 11 in its fixture. Other fixed holder arrangements could include clamping or other mounting applications to form a fixed reference for measurement purposes, aligned to wherever the center of the emission will be.

In accordance with the invention, the present invention for the array tester 10 may further include a fixed or movable portion 16 of the measurement system for moving in at least one relative direction, angularly vertically 21, angularly horizontally 22, or laterally horizontally in one of two orthogonal directions 23 or 23' with respect to the laser array 11 for at least polarization-resolving and optionally including wavelength-resolving an optical measurement of the individual ones of the semiconductor devices as a function of the at least one relative direction 21, 22, 23, or 23'. The movable portion 16 of the measurement system minimizes alignment and tolerance problems and provides a fast, flexible, and accurate characterization of the array 11.

Figure 3:
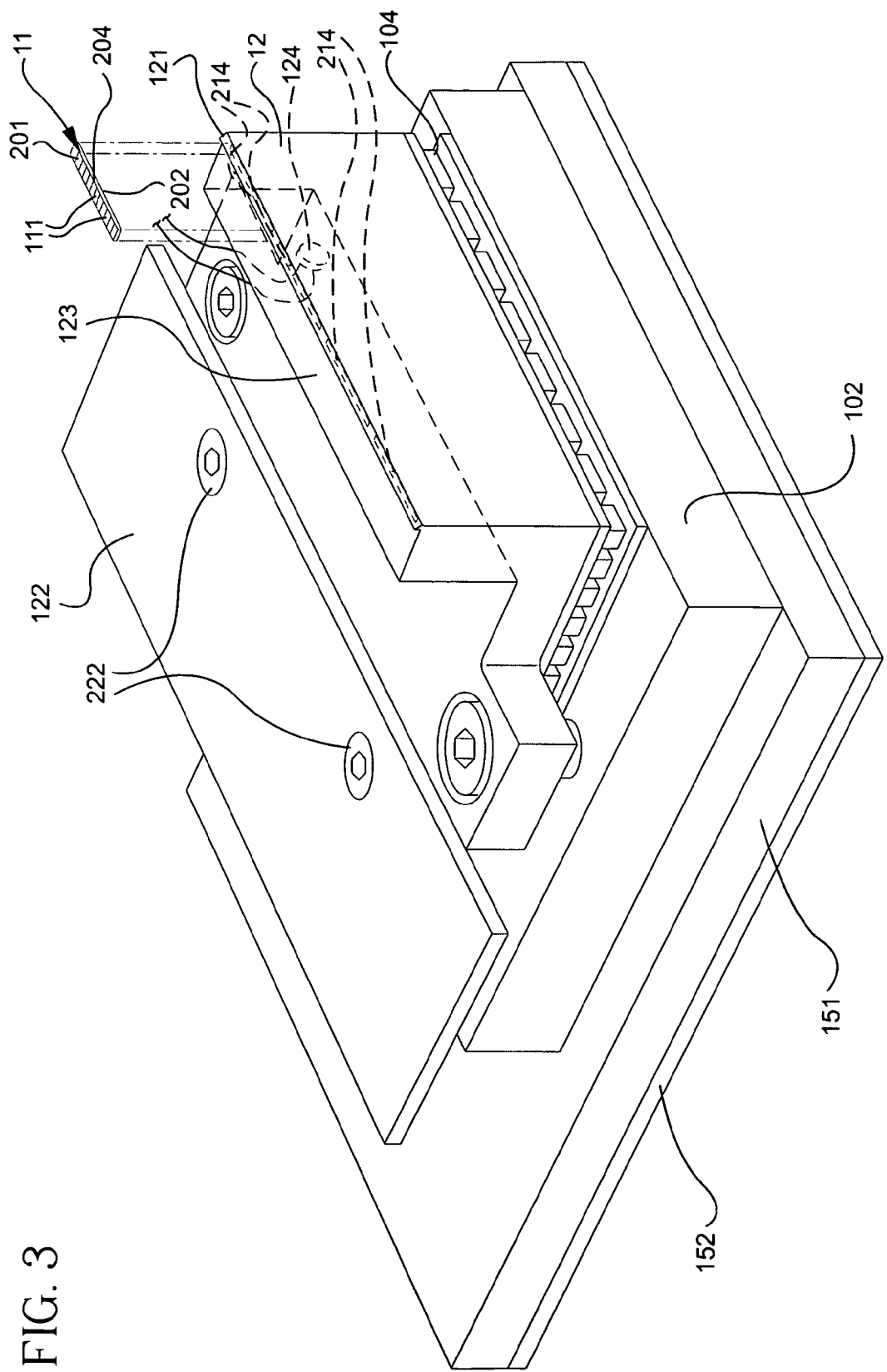
FIG. 3 is a blow-up perspective portion of the vacuum held and temperature controlled array assembly and array of FIG. 2, in accordance with the present invention.
Figure 4:
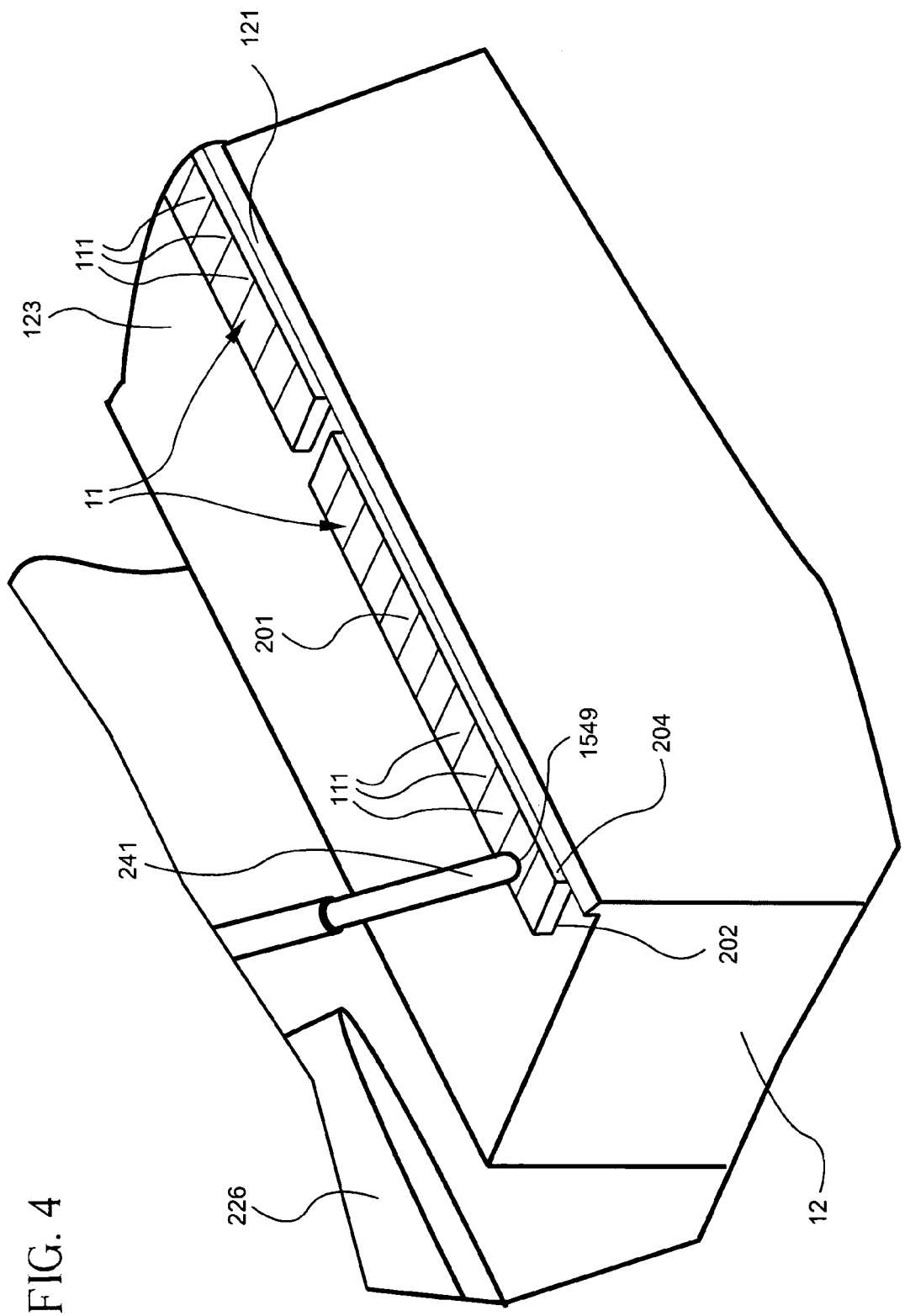
FIG. 4 is a blow-up perspective drawing of the vertically movable probe pin 241 of FIG. 3 for contacting the selected device at the preselected indexed position, in accordance with the present invention.

As embodied herein, and depicted in FIG. 1, the movable portion 16 of the measurement system includes a prober or probing fixture 24 for selectively probing a selected device of the array 11 in a selected fixed position, defined by the probed position. The movable portion 16 of the measurement system is capable of making optical measurments by selectively using appropriate detectors or other characterisers and fixedly using them or alternatively, moving them around the selected device 111 of the array 11, as seen in FIGS. 2-4, to make the desired measurement.

Figure 2:
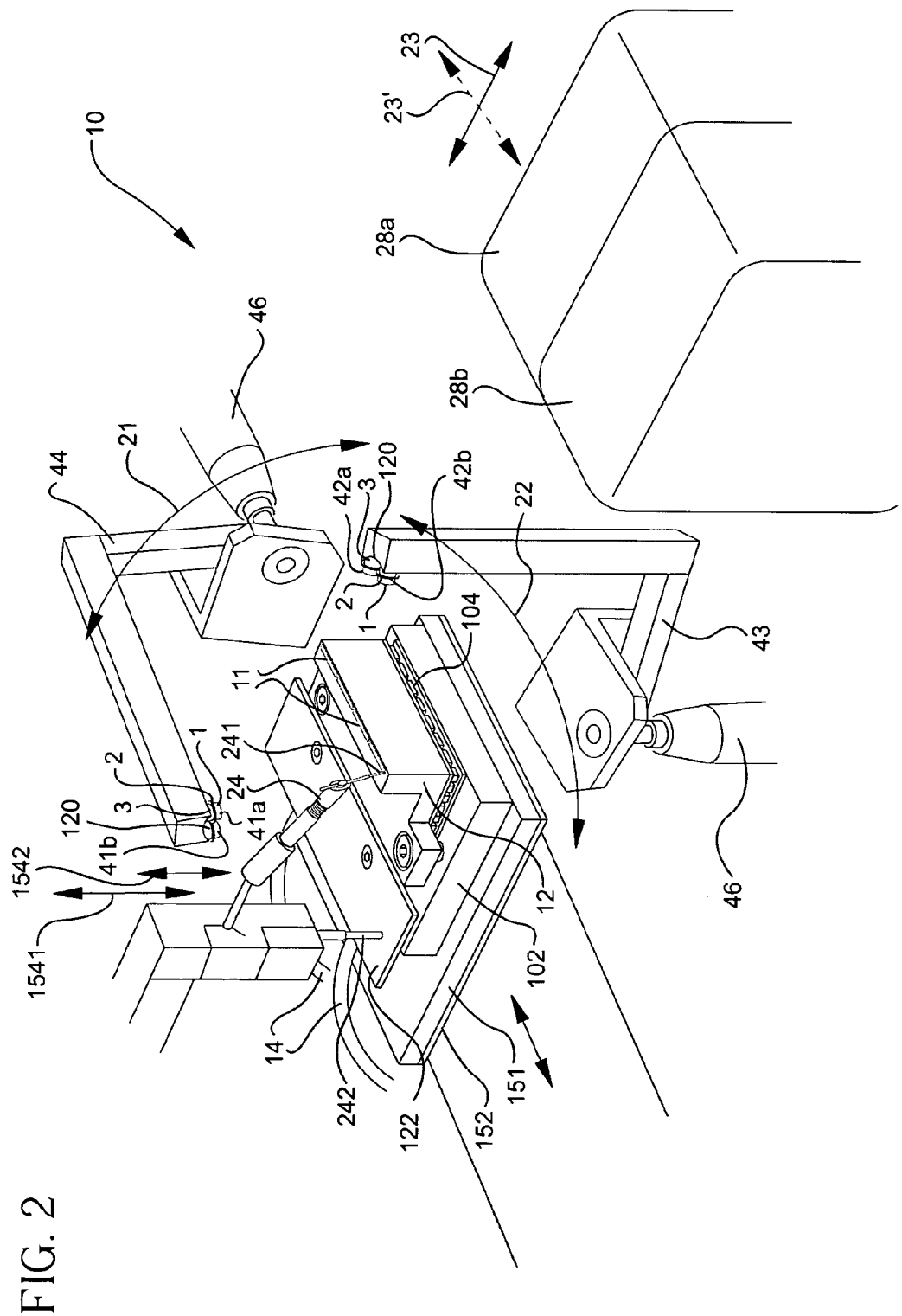
FIG. 2 is a blow-up perspective portion of the vacuum held and temperature controlled array assembly, held array, and prober of FIG. 1, with reference to the far-field scans of FIG. 1, in accordance with the present invention.
Figure 5:
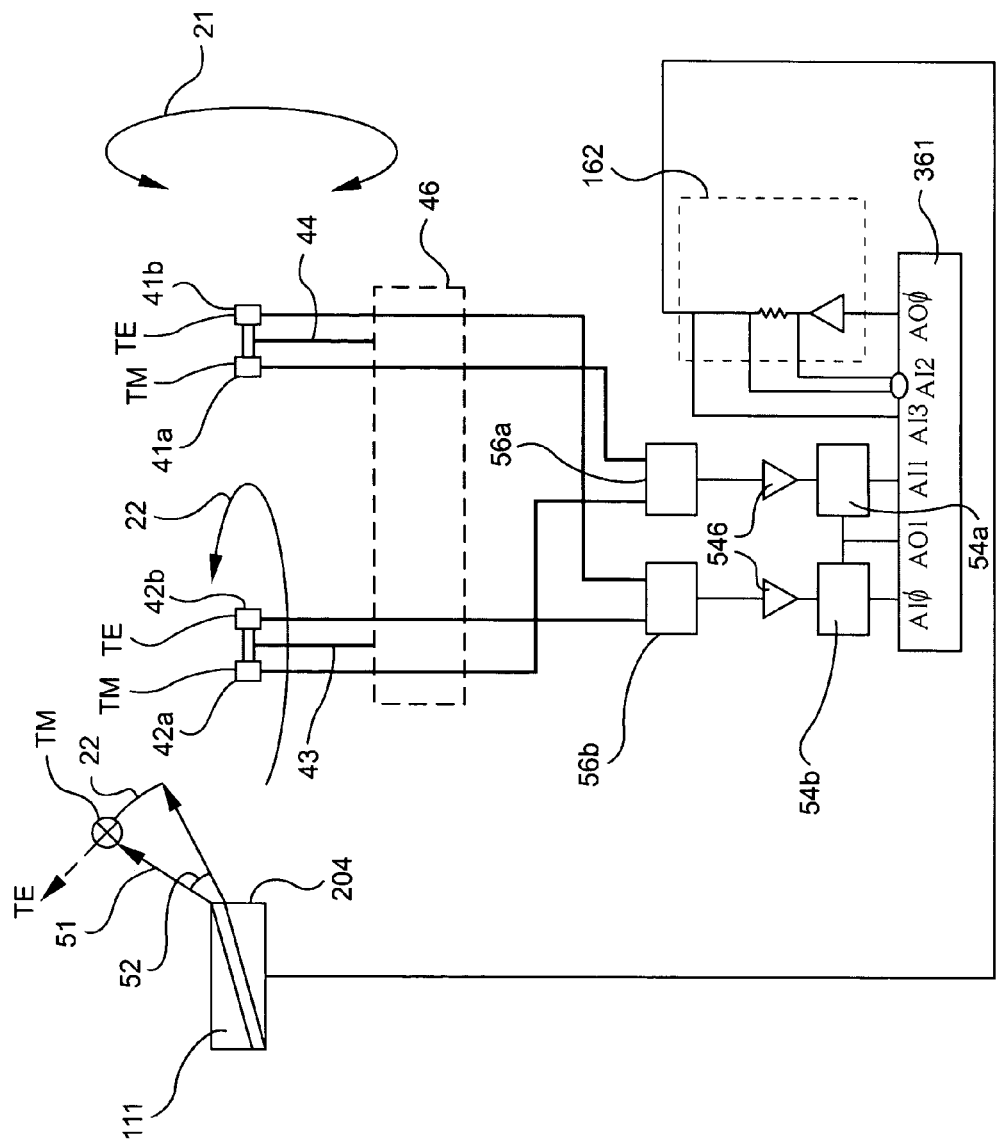
FIG. 5 is an electrical lay-out representation of the TM and TE far-field measurement characterizers, in a somewhat mixed side-view representation, and a top-view representation of a tilted-facet SOA measured by the characterisers, as an example of the operational relationships of FIG. 1, in accordance with the present invention.

For example, as seen in FIGS. 1, 2, and 5, at least two pairs of transverse magnetic (TM) and transverse electric (TE) detectors 41a-b and 42a-b is provided for collecting a TM and TE far-field measurement of the emission 51 from the selected device. As is known and shown in the top view portion of FIG. 5, emission 51 is made-up of two orthogonal components, the TE-polarization component and the TM-polarization component. These components are represented by their electrical fields.

Each of the detectors or optical characterizers 41a, 41b, 42a, and 42c has an optional narrowband wavelength-selective filter 1, a polarization-selective filter 2, and a photodetector 3 even though not all parts may be visible or labeled for simplifying the drawings. The polarization-selective filter 2 can be a polarization splitter or polarizer for selecting the TM polarization vectors to transmit to the photodetector 3 to form a TM photodetector. On the other hand, the polarization-selective filter 2 can be the same polarization splitter or polarizer, displaced from the TM filter by ninety degrees, for selecting the TE polarization vectors to transmit by the photodetectoer 3 to form a TE photodetector. Hence, the TE polarizer only transmits the TE-polarization component while the TM polarizer only transmits the TM-polarization component. In some applications, the detector can be fixed with a TM or TE polarizer selectively moved in front of the detector for measuring TM and TE polarization measurements one at a time or simultaneously.

Instead of a pair of separate polarizers 2 for TM and TE, a beamsplitter arrangement, or other known variations can be optically aligned to transform the beam received into a TM and a TE mode. As another variation the same polarizer can be simply moved for the TM polarization measurement and displaced ninety degrees for the TE measurement.

Optionally, the narrowband wavelength-selective filter 1 can be further included as a narrow bandpass filter, to be placed in front of the polarizer, for transmitting wavelengths $\lambda$ to the photodetector 3 in a bandwidth between $\lambda-\Delta\lambda/2$ to $\lambda+\Delta\lambda/2$ as a wavelength-resolved measurement. Even though the narrow band filter 1 is shown in front of the polarizer 2 for covering the receiving opening of the photodetector 3, the order can be changed in other embodiments. Preferably, $\Delta\lambda$ is about 2 nm.

If a movable polarization-resolved system is used, a first motor-driven arm 43 moves a first pair 42a-b of the TM and TE detectors in a horizontal arc path 22 relative to the selected device to sample the horizontal far-field. Similarly, a second motor-driven arm 44 moves a second pair 41a-b of the TM and TE detectors in a vertical arc path 21 relative to the selected device to sample the vertical far-field. Preferably, for better angular alignment with the emission of the selected device 111, the pair of TM and TE detectors are each radially aligned in an arcuate mounting arrangment 120, as seen in FIG. 2. In this manner, it is appreciated that the optimum alignment with the center of the emmission will be achieved. Known off-setting procedures can be used to take care of tolerances or off-axis alignment.

Correspondingly, if the device, such as an SOA, has a tilted facet away from a centerline, the vertical far-field arm is preferably positioned at an off-set angle to be able to capture the full vertical field from the center of the emission that was displaced from the centerline. Likewise, the horizontal far-field arm is preferably positioned at another suitable off-set angle to be able to capture the full horizontal field from the center of the emission that was displaced from the centerline.

Referring to FIGS. 1, 2, and 5, a programmable motor or another suitable motion controller 46 actuates the arms 43 and 44. However, the arms 43 and 44 can be moved by other electrical or mechanical mechanisms. The movable portion 16 of the measurement system uses two mini-motor driven arms 43 and 44 to move the two pairs of pin-size photo TM and TE detectors 41a-b and 42a-b, one set on each arm 43 and 44, to sample across both the horizontal and vertical far-fields 21 and 22. An encoder on the motor of the motion controller 46 allows positioning the detectors 41a-b and 42a-b with high accuracy (within 0.02 degree) and a preamplifier, such as trans-impedance amplifier 546, each in electrical path of the detectors 41a-b and 42a-b guarantees a large dynamic gain range for each of the detectors 41a-b and 42a-b. The size of each of the detectors 41a-b and 42a-b is chosen to be about 100 um in diameter, and the distance from one of the detectors 41a-b or 42a-b to the chip's edge 204 is about 60 mm. The angular far-field resolution is estimated to be about 0.2 degree.

For all optical measurements, the contacted array 11 and a contacting probe tip 241 are maintained still in a fixed position. One preferred example of an optical measurement is the far-field scan which is very important in characterizing beam quality. Usually a semiconductor chip has an elliptical beam shape in its emission 51 because the width of the waveguide is usually larger than the thickness. Therefor a complete characterization of the far-field requires scanning across the divergent beam 52 along two orthogonal axes 21 and 22.

The bar or array tester 16 so far described is much cheaper to build and to maintain than the traditional fiber-fiber system. This bar tester design uses only standard electronics and optics components and the alignment between the devices 111 and the far-field detectors 41a-b and 42a-b, although very critical, is made easy because of the relative large distance between them.

In summary, a pair of TM and TE detectors 41a-b and 42a-b are mounted on each far-field arm 43, 44. Each photodetector 3 is covered by a polarization filter 2 to select either TE or TM polarization to transmit. Each photodetector 3 is also covered by a bandpass filter 1 to transmit wavelength only in $(\lambda-\Delta\lambda/2, \lambda+\Delta\lambda/2)$. For example, $\Delta\lambda$ can be approximately 2 nm.

Referring to FIG. 5, a synchronization detection scheme is adopted to remove background noise and improve signal to noise ratio. An analog-to-digital (A/D) or data acquisition (DAQ) card or board 361 is used to sample the far field emission. The portion of emission received is dependent on a the particular vertical or horizontal angle received by each of the TM and TE photodetectors 41a, 41b, 42a, and 42b. The photocurrent generated by the corresponding detector is amplified and converted to voltage by the corresponding trans-impedance amplifier. The voltage signal from the trans-impedance amplifier is fed to one of two corresponding TE or TM lock-in amplifiers 54a or 54b, respectively. These lock-in amplifiers 54a and 54b are synchronized with the modulation frequency provided in the output channel AO1 of the DAQ board 361. The modulation frequency modulates the amplitude of the injection current supplied to the selected device 111 by the modulated current supply module 162. The current supply module 162 is controlled by the output channel AO0 of the DAQ board 361, as processed by the controller 36. This synchronization detection scheme is used to remove background noise and improve the signal-to-noise ratio of the measurement system 16. The amplitude modulation of the injection current is preferably at about 500-HZ and the lock-in amplifiers 54a are 54b are synchronized with the current modulation at this same 500-Hz frequency by the trigger signal available on the output channel AO1 of the DAQ board 361. Current under this modulation frequency is a quasi-CW current. The maximum amplitude of the injection current is varied by the DAQ board 361 so that polarization-resolved and wavelength-resolved far-field patterns are measured at different injection levels, as shown in the four graphs of the horizontal TE farfield (FF), vertical TE FF, horizontal TE FF, and vertical TE FF of FIG. 7. However, other modulation frequencies, other than 500-Hz are also feasible, such as 2 kHz.

As an example of a possible electrical lay-out, a fast DAQ board 361 is used to provide the current modulation signal through channel AO0 to the current amplifier inside the modulated current supply module 162. The amplitude of the current output from the current amplifier of the current supply module 162 is proportional to the amplitude of the modulation signal. Each far-field's photocurrent, detected by the set of TM and TE detectors 41a, 41b, 42a, and 42b, is selected by a 2×1 electrical switch 56a or 56b and amplified by a transimpedence amplifier 546. Each of the output of transimpedence amplifier 546 is fed to one of the two corresponding lock-in amplifiers 54a or 54b. The outputs of the lock-in amplifiers 54a and 54b are then fed to the DAQ board 361 on channels AI0 and channel AI1. The voltage across the 2-Ohm resistor, inside the current supply module 162, is measured by the DAQ board 361 on channel AI2 to calibrate the current injected into the selected device or chip 111.

The controller 36 reads the board 361 on channels AI0 and AI1 to obtain the TM and TE far-field emission detected as the output from each of the lock-in amplifiers 54a and 54b, respectively. Controller 36 also is controlling the outputs of the board 361 on channel AO0 to the current supply module 162 to vary the amplitude of the modulated current injection. Furthermore, the controller 36 controls the stepper, indexed, or otherwise controlled motor 46 whereby the vertical or horizontal angle can be stepped axially or radially through a predetermined sequence to change the photodetector's acceptance angle where $\theta$ is the horizontal angle and $\psi$ is the vertical angle, for the horizontal direction and vertical direction, respectively.

During measurement, light of narrow spectral width as passed by each of the narrow bandpass filter 1 and polarized by one of the TE or TM filter 2 reaches the aperture receiving window of each of the corresponding TM or TE detector 41a-b and 42a-b. Only a certain angular fraction of the total three-dimensional output light emission 51 or total power (P) is directed onto the apertured receiving window of the photodetector 3 and this produces an electrical output which is amplified before being directed to the controller 36. At the controller 36, a detected light corresponding to the photodetector 3 apertured window receiving position and thus to a predetermined positioning angle $\theta$ and $\psi$ is measured. The incidence power on detector 3, within $(\lambda-\Delta\lambda/2, \lambda+\Delta\lambda/2)$ and of one polarization (TM or TE), versus the far-field angle is recorded.

Far-field patterns are defined as the angular dependence of optical intensity or power for a laser, from the emitting cleaved facet or the angular dependence of amplified spontaneous emission (ASE) for an SOA.

Because the emission from most lasers are coherently emitting at a narrow optical frequency and singularly polarized (TE polarization only), the wavelength-resolved and polarization-resolved aspects of the present invention are not as needed for a laser as for an SOA. However, if a laser with both TM or TE modes are desired, the equations for the laser can be similarly derived for the laser case as will be used for the SOA case.

When different polarization modes occur, the far-field patterns for each TE and TM must be measured. Furthermore, far-field measurements can be taken at different current levels.

For an SOA, polarization-resolved and wavelength-resolved total ASE power is the integration of polarization-resolved and wavelength-resolved far-field patterns. The far-field pattern is measured for the emissions, in this case, the ASE, over a wavelength range ($\lambda-\Delta\lambda/2, \lambda+\Delta\lambda/2$) and for TE and TM polarization.

The TE-polarization far-field pattern, intensity versus angle, is written as:

$$H_{TE}(\theta) = A_{TE} \cdot h_{TE}(\theta) \quad (1)$$

$$V_{TE}(\psi) = A_{TE} \cdot v_{TE}(\psi) \quad (2)$$

for horizontal direction and vertical direction, respectively, where $\theta$ is the horizontal angle and $\psi$ is the vertical angle, and $h_{TE}(\theta)$ and $v_{TE}(\psi)$ are normalized functions with maximum values equal to 1, $A_{TE}$ is the maximum intensity for TE.

The two-dimensional (2-D) far-field pattern of TE polarization in angular domain ($\theta,\psi$) is then, taught by the present invention to be $$F_{TE}(\theta,\psi) = A_{TE} \cdot h_{TE}(\theta) \cdot v_{TE}(\psi) = A_{TE}^{-1/2} H_{TE}(\theta) \cdot A_{TE}^{-1/2} V_{TE}(\psi) \quad (3)$$

Integrating over the horizontal angle $\theta$ and the vertical angle $\psi$ gives the total ASE power for TE in wavelength range ($\lambda-\Delta\lambda, \lambda+\Delta\lambda$):

$$P_{ASE}(\Delta\lambda,\lambda)_{TE} = \oiint F_{TE}(\theta,\psi) d\theta d\psi = A_{TE}^{-1/2} \oint H_{TE}(\theta)d\theta \cdot A_{TE}^{-1/2} \oint V_{TE}(\psi)d\psi \quad (4)$$

Similarly, for TM polarization $$P_{ASE}(\Delta\lambda,\lambda)_{TM} = \oiint F_{TM}(\theta,\psi) d\theta d\psi = A_{TM}^{-1/2} \oint H_{TM}(\theta)d\theta \cdot A_{TM}^{-1/2} \oint V_{TM}(\psi)d\psi \quad (5)$$

Therefore, to calculate the total ASE power for TE in the desired wavelength range ($\lambda-\Delta\lambda/2, \lambda+\Delta\lambda/2$) one needs to know the TE vertical far-field pattern, $V_{TE}(\psi)$, the TE horizontal far-field pattern $H_{TE(\theta)}$ and the maximum value $A_{TE}$.

The same is applied to the total ASE power for TM in the desired wavelength range ($\lambda-\Delta\lambda/2, \lambda+\Delta\lambda/2$). The calculated totals are shown in the TE ASE and TM ASE curves versus current graphs of FIG. 7. These TE ASE and TM ASE curves are calculated from the 4 Horizontal/Vertical TE/TM FF curves of FIG. 7. Furthermore, far-field measurements can be taken at different current levels as seen in the intensity graphs of FIG. 6-7, where the TE curves usually have wider shoulders than the TM curves. Thus, the total ingrated ASE power, within ($\lambda-\lambda/2, \lambda+\lambda/2$) and of one polarization (TM or TE), is found as a function of injection current.

Figure 6:
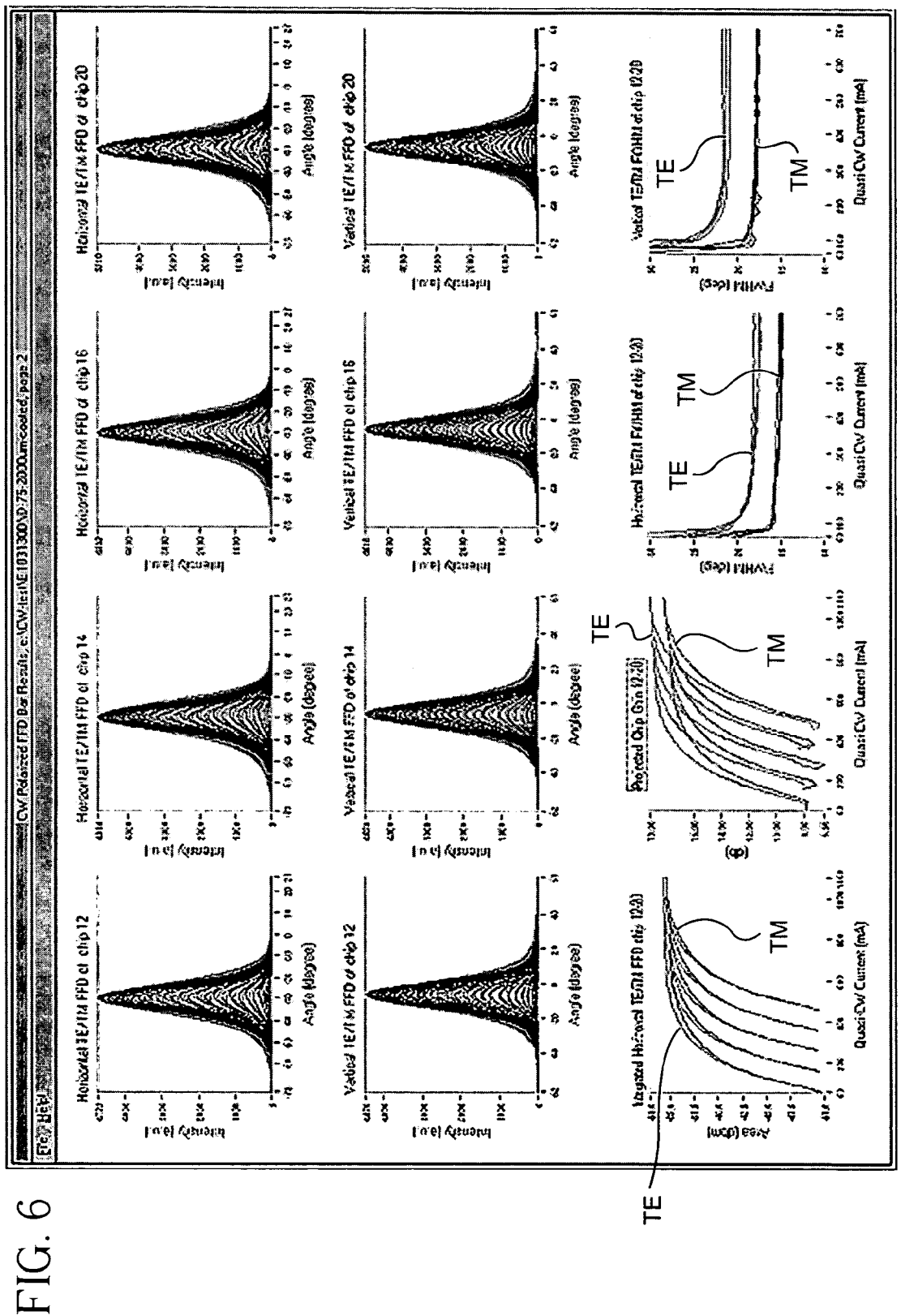
FIG. 6 is a display of various optical measurement graphs generated by the tester of FIG. 1, in accordance with the present invention.

The near-field mode-field diameter (MFD) is another important parameter for chip design and estimation of fiber to chip coupling efficiency, in general. Since the near-field pattern is the Fourier transform of the far-field pattern and vise versa, the wavelength-resolved and polarization resolved far-field patterns are also used to estimate the near-field patterns for a particular polarization and wavelength. If the far-field and near-field patterns are both Gaussian, then the near-field mode-field diameter can be approximated by $$MFD = \frac{2\lambda}{\pi \tan(0.85 * FWHM)}$$

where FWHM is the full-width-at-half-maximum angle for a far-field pattern at a particular wavelength and polarization and can be seen in the horizontal and vertical FWHM versus quasi-continous wave current graphs of FIG. 6.

After the total integrated ASE power is known from the area graph of FIG. 6, other chip parameters can be determined. For example, the chip gain can be calculated from the total integrated ASE power as it is related to the ASE by an appropriate factor. As already known, the ASE power of a SOA is derived as (with possible intervening formulas 6-9 not shown):

$$P_{ASE} = \frac{\Delta\omega \cdot \omega \cdot n_{sp} \cdot [G(\omega)-1]}{2\pi\eta} \hbar \quad (10)$$

where $\omega$ is angular optical frequency and $\Delta\omega$ is the sampling interval, $n_{sp}$ is population inversion factor and $\hbar$ is quantum efficiency, $\eta = (g-\alpha)/g$ where g and $\alpha$ are material gain and waveguide loss, respectively.

Under sufficient current injection, $n_{sp}$ and $\eta$ are constants independent of current injection, in wavelength domain equation (10) is simplified as $$G(\lambda) = C(\Delta\lambda,\lambda) \cdot P_{ASE}(\Delta\lambda,\lambda) + 1 \quad (11)$$

where $C(\Delta\lambda,\lambda)$ is a coefficient depending on wavelength.

Including the polarization dependence, equation (11) is expressed as:

$$G_{TE}(\lambda) = C_{TE}(\Delta\lambda,\lambda) \cdot P_{ASE}(\Delta\lambda,\lambda)_{TE} + 1 \quad (12)$$

$$G_{TM}(\lambda) = C_{TM}(\Delta\lambda,\lambda) \cdot P_{ASE}(\Delta\lambda,\lambda)_{TM} + 1 \quad (13)$$

Equations (12-13) form the basic of projecting optical gain from ASE power measurement. Both ASE power and Gain are polarization and wavelength dependent. Coefficients $C_{TE}(\Delta\lambda,\lambda)$ and $C_{TM}(\Delta\lambda,\lambda)$ can be calculated but more conveniently found experimentally by correlating ASE power and chip gain that is, for example, measured with traditional the fiber-fiber system.

The difference between $G_{TE}(\lambda)$ and $G_{TM}(\lambda)$ is called the polarization-dependent gain (PDG). Applying Equations (4), (5), (12) and (13) to the far-field patterns at many current levels, the gains are measured as functions of current.

Referring to FIG. 6 there is shown a screen-shot of an example of the TM and TE lines of optical SOA bar measurements, with various parameters displayed for individual characterized chips processed in accordance with the teachings of the present invention. The bar testing process of SOA is characterized for all of the chips of the multiple bars.

Figure 7:
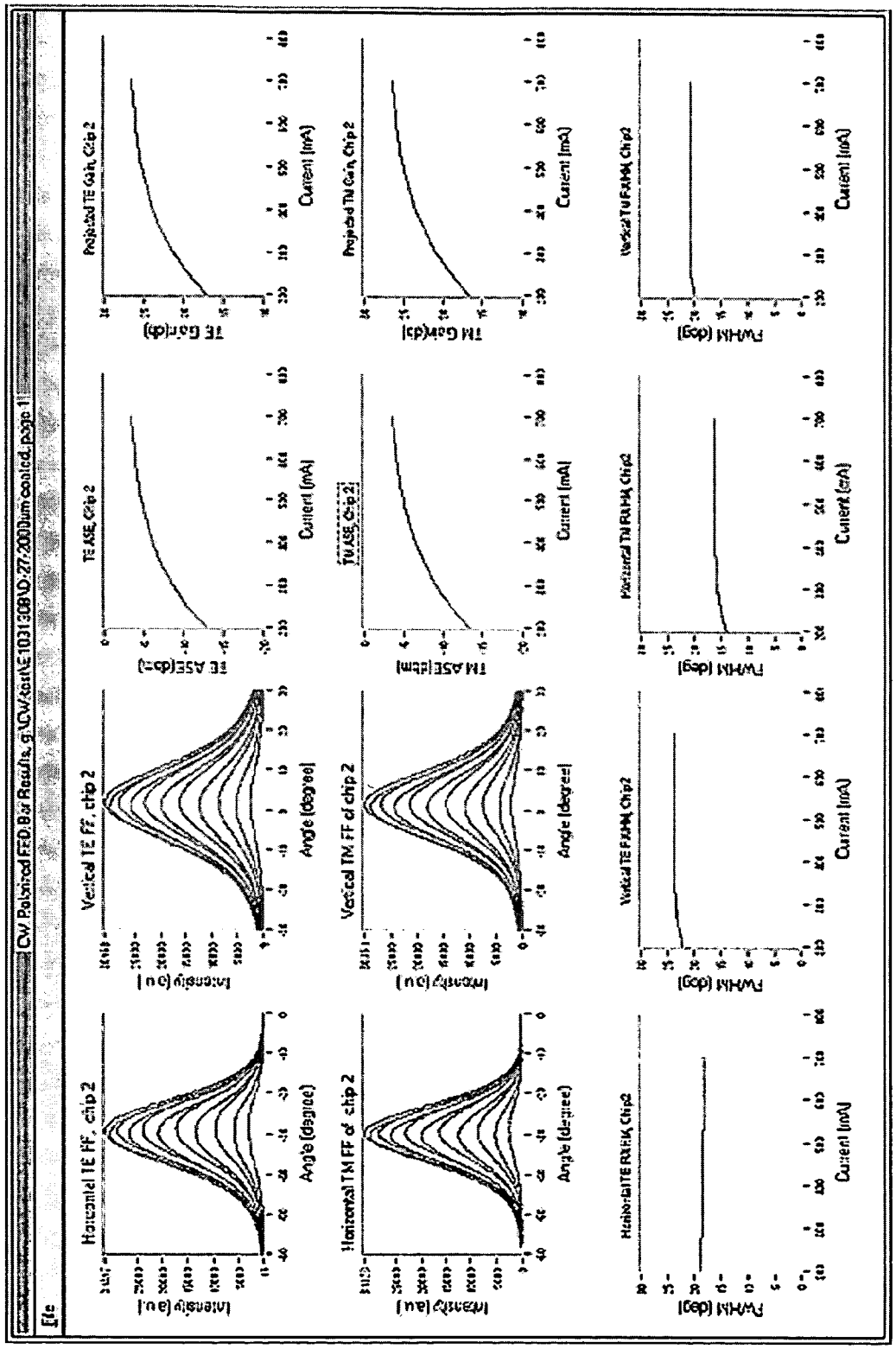
FIG. 7 is a broken-down display of one chip with a different design and different wavelength than the ones characterized in FIG. 6, in accordance with the present invention.

Referring to FIG. 7, the individual curves for one chip of a different design and wavelength are shown instead of for a few chips as shown together in FIG. 6. The TE and TM curves are also separated into different plots to illustrate their differences.

SOA bars are loaded onto the vacuum chuck. Multiple bars are accommodated at the same time. The control software positions one of the SOAs underneath the contact probe and the contact prober is lowered to make the contact.

The control software sends a train of modulated signal with correct amplitude and frequency to the current amplifier; the current amplifier's output is applied to the SOA. The horizontal far-field arm 43 makes a scan, both TE far-field pattern $H_{TE}(\theta)$ and TM far-field pattern $H_{TM}(\theta)$ are collected. The vertical far-field arm 44 makes a scan, both TE far-field pattern $V_{TE}(\phi)$ and TM far-field pattern $V_{TM}(\phi)$ are collected as seen in the intensity versus angle plots in FIG. 7. $V_{TE}(\phi)$ and $V_{TM}(\phi)$ are normalized to calculate $v_{TE}(\phi)$, $A_{TE}$, $v_{TM}(\phi)$, and $A_{TM}$ where $A_{TE}$ and $A_{TM}$ are the maximum values for the functions. Equations (4-5) are used to calculate the ASE power. This process is repeated for many current levels Equations (12-13) are then used to calculate the gain. This process is repeated for many current levels to plot the chip gain as a function of current as seen in the projected chip gain versus current graph of FIG. 7.

Another exemplary application of far-field patterns is for gain-tilt determinations. If at least a second narrow bandpass filter having a different desired wavelength $\lambda_2$ than the first narrow filter 1, is used together with the first filter 1, then the wavelengths transmitted in the second bandwidth approximately between $\lambda_2 - \Delta\lambda_{2/2}$ to $\lambda_2 + \Delta\lambda_{2/2}$ of the optical output or emission 51 compared to the bandwidth of the first wavelength filter 1, can be compared at different wavelengths for optically characterizing the difference as a gain-tilt. By adding more detector pairs that are covered with bandpass filters 1 of different transmisive wavelength, the gain at different wavelengths can be measured; the gain tilt, defined as the difference of gain across a wavelengths range, can accordingly be characterized.

It is noted that equations (12-13) do not specify how the polarization-resolved and wavelength-resolved ASE power is measured. One effective technique, as taught in this invention, is the far-field measurement. However, other techniques are also taught.

Another method is to measure polarization-resoveld power by using polarization filters 2 and a large-area photo detector than the smaller photodetoector 3. Polarization filters 2 are mounted on a translational stage. To measure TE-polarization ASE, the TE-polarization filter 3 is moved to be between the SOA's output facet and the large-area photo detector. To measure TM-polarization ASE, TM-polarization filter is moved to be between the SOA's output facet and the large area photo detector. The distance between the polarization filter 2 and the SOA's output facet should be as small as possible to make sure light beam from the SOA is being completely covered by the aperture of the polarization filter 3.

Another method to measure wavelength-resolved ASE power is by using a wavelength-selective filter 1 and the large-area photo detector to measure the optical signal. Another example is to use a multimode fiber to collect light and send the optical signal to an optical spectrometer analyzer (OSA) 52. These alternative methods can be faster in testing SOA devices than the far-field measurement technique since the parts are stationary except when the polarization filters 2 and narrow bandpass wavelength filters 1 are moved by the translation stage. However, for SOAs having large optical angular divergence, if the polarization filters 2 and wavelength filters 1 are planar, then the polarization and wavelength selectivities are negatively impacted.

As another example of an optical characterizer, an optical spectrum analyzer (OSA) 52 is connected to an integrating sphere 28 and a controller 36 for providing optical spectrum analysis, as seen in FIG. 1.

To complete the optical spectrum analysis, the measurement system 16 automatically records wavelength of the emissions 51 of the selected device 111 at different current levels programably supplied by a current supply 162.

As another optional portion 16 of measurement system, a slidable integrating or intergration sphere 28 is connected to a slider 32 for laterally moving, in one of two possible orthogonal horizontal directions 23 or 23', towards the selected device 111 for collecting an emission 51. The integration sphere 28 is able to measure all emissions 51 from the selected electro-optical chip 111. If the beam divergence 52 is sufficiently small, a pair of TM and TE integration spheres 28*a-b* can each be used with a similar set of the already discussed polarization filter 2 and wavelength filter 1 to replace the first and second set of TM and TE detectors 41*a-b* and 42*a-b*.

For use with an SOA as the semiconductor device 111, the pair of integrating spheres 28*a-b* laterally move, in one of two orthogonal directions, 23 or 23', towards the selected SOA for collecting an amplified spontaneous emission (ASE).

Referring to FIGS. 1-4, an enlargement of the array 11 of FIG. 1 is shown in FIGS. 2-4, with reference to particular portions of the measurement system 16 of FIG. 1. A properly designed array fixture provides a method of easy loading and unloading arrays, a method of providing good electrical conductivity and a method of controlling temperature.

To provide a more accurate array measurement system, the temperature is controlled and monitored as close to the array 11 as possible. A reference of portions of the array, in its vaccuum holder 12, to portions of the measurement system 16 is first described to show where the measurements are referenced or indexed from. As seen in FIGS. 3-4, the P-contact surface 201 of the semiconductor array 11 is facing upward for the prober 24 to access. The output edge 204, such as an emitting facet of a laser or side of an SOA, of the array 11 is near a stop block feature 121 located on top of a base portion 123 of the holder 12 of FIG. 1 for facilitating array alignment while enabling measurements, such as the far-field scans along the arc paths 21 and 22 as seen in FIG. 2.

A first one of a pair of probes of the prober 24, the probe tip 241, preferably flexible, makes contact to the top surface 201 of the laser array 11, as seen in FIGS. 1-2. This single reference point of the probe tip 241 will be used as the fixed reference for all optical measurements.

The other probe, a ground probe 242, makes contact to a striker plate 122 as the electrical ground. For greater flexibility, in case the surfaces of the laser array 11 is uneven, the probes 241 and 242 are preferably each in the form of a flexible pin, such as a pogo-pin. One advantage of having such a double-probe design is the minimization of microwave reflection when doing pulsed current operation for certain array testing measurements.

Referring to FIG. 3, the striker plate 122 is on the opposite side of the stop block feature 121 to mount the array 11 in the holder 12 between the elevated stop block feature 121 and the striker plate 122. Plated with a layer of gold for good electrical conductivity, the striker plate 122 is physically and electrically attached to the base portion 123 of the holder by screws 222. An advantage of using a separate striker plate, other than the base portion 123 of the holder for probing, is that a smaller worn-out striker plate need only be replaced instead of a complete, bigger, and more complexed holder 12.

The N-contact 202 of the laser array 11 is electrically and thermally grounded to the base portion 123 of the holder 12, preferably implemented as a gold plated fixture. A thermoelectric cooler 104 and a heat sink 102 are added underneath the vacuum holder 12 to control the temperature surrounding the array 11 under testing, as seen in FIGS. 1-3.

Referring also to FIG. 4, the temperature is monitored with the temperature controller module 126 fed by the thermal signals picked-up by a thermal sensor 124 mounted inside the holder 21 for feeding-back temperature near the array 11. Preferably, the temperature is controlled by a computer module, referenced as the temperature controller 126, for regulating the testing temperature in the range of −20 to 80 degrees C.

To provide a fixed and indexable position for the array 11, the vaccuum holder 12 for the array 11 of FIG. 1 is shown in more detail in FIGS. 2-3. The array 11 is preferably held by the vaccum suction 14 applied through a vacuum slot 214 in the base portion 123 of the holder or fixture 12. By turning or activating the vacuum switch 114 of FIG. 1 "ON" or "OFF", as controlled by the controller 36, the array 11 can be easily loaded to or unloaded from the holder 12. Preferably, four arrays 11 are mounted at the same time, thus down-time due to loading/unload is minimized. For simplicity, only one array 11 is shown in FIG. 3.

The front edge of the vacuum holder 12 has a triangular-shaped protrusion used as a stop block feature 121 to position the array 11 on the output side 204. An appropriately designed tool (not shown) pushes the array 11 against the stop block portion 121 of the holder and aligns the array 11 into an indexable position on top of the base portion 123 of the holder. The height of the stop block portion 121 is preferably designed such that the active top region of the array 11 is about 50 um above the top point of the stop block 121 to protect the array from contact damage. Arrays 11 are loaded to the testing system 16 in situ or in batch process, that is, the chuck or holder 12 is not relocated to a remote location for loading/unloading. This in situ procedure not only minimizes the down time of the system but also allows automatic loading/unloading.

Referring to FIGS. 1-4, the individual chips or devices 111 on the array 11 are indexed by a probing mechanism or system consisting of a horizontal motorized X-stage 152 which is supporting the array holder 12 above through the use of an adapter plate 151 that is mounted to the X stage 152 and the prober 24, already described having dual probes in a probe tip assembly, that is connected to a vertical motorized Y-stage 154. Controlled by the motion controller 36, the X stage 152 horizontally moves the array 11 which is placed on top of the X stage 152, as seen in FIGS. 1-2. To move individual devices or chips 111 of the array 11 into or out from the indexed measurement position, the horizontal X-stage 152 translates the array fixture or holder 12 with respect to the tip of the probe tip 241. While a chip 111 is in the measurement position, the vertical stage 154 lowers the probe tip 241 to make the electrical contact and measurements are taken. After a chip 111 is fully characterized, the vertical stage 154 of FIG. 1 raises the probe tip 241 off the device surface 201 and waits for the next device to move in. Also controlled by the motion controller 36, the vertical stage 154 is raised and lowered every time a specfic device 111, one of the many chips 111 on the array 11, is translated or indexed next, underneath the probe tip 241 for testing. The probe tip, as part of the prober 24, is attached only to the Y stage 154 for minimizing the movement of the laser array 11. Once a device 111 is moved underneath the probe tip 241, the prober 24 is lowered to make contact and all the other characterizers, such as detectors, move around that particular laser 111 for various measurements. This procedure repeats itself until all the chips 111 on the array 11 are tested.

One of the key issues in probing is how to avoid scratching the device surface 201 by the probe tip 241. The probing system manages to create no scratch marks by using an inventive step-and-check or step-approximation approach. The software in the controller 36 that controls the probing system moves the vertical stage 154 towards the top array surface 201 in small increments or small steps 1541 that get even smaller 1542 as the expected contact is approached, as seen in FIG. 2. Preferably, the testing software is facilitated by the controller 36, implementable using a Pentium computer, that is also capable of performing optical tests, in the form of various modules 162, and 126 as seen in FIG. 1. At each increment, the software in the controller 36 checks if there exists a close electrical loop between the array 11 and the associated electronic instrument, such as whether the current supply 162 can pass a current to enable the current to be read. A contact position 1549, as seen in the magnified representation of FIG. 2 in FIG. 4, is obtained when such a close loop is found, for example, when a current measurement can be read. The controlling software in the controller 36 also calculates the parameters of the array surface plane, such as the location of the next expected contact point, based on devices 111 that have been successfully probed; these parameters are used to help obtain a faster contacting approach time for the rest of the chips 111 on the array 11. This step-wise contacting approach also allows successful probing on rough or uneven laser array surfaces.

Referring back to FIG. 1, all of the other detectors or characterizers, such as the slider 32 for the integrating sphere 28 are also aligned to the position where the probe tip 241 is lowered for making contact with the selected chip 111. This position was determined when the system was initially setup. Each of many individual chips 111 on an array 11, is moved to that same initial setup position for test. Therefore, the proper alignment of individual chip 111 with all the detectors is preserved.

In summary, teachings of the present invention of a bar or array tester to measure polarization- and wavelength-resolved light-output of an electro-optical device, is especially useful for SOAs. Both the polarization-resolved far-field TM and TE pattern of an electo-optical device is measure while the far-field pattern is also wavelength-resolved. This scheme to calculate the polarization- and wavelength-resolved light output power of an electo-optical device from far-field patterns can be applied to calculating the amplified spontaneous emission (ASE) power of an SOA in order to calculate polarization- and wavelength-resolved chip gain. Polarization and wavelength resolved mode-field diameter is estimated from far-field patterns.

Hence, the resultant SOA bar tester has the advantages of efficiency and low-cost over traditional fiber-fiber system. The inventive system tests SOA device at an early stage during fabrication, therefore it is an efficient tool for quality control. By testing SOA devices on bar forms; this is a batch testing process with high throughput. No input or output fibers are used since the SOA's own ASE is measured so there is no need for fiber alignment or problems because of misalignment. High throughput results of a few minutes per device compared to hours per device in the fiber-to-fiber system.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A tester for screening of individual chips of an electro-optical array, the tester comprising:
   a holder for securing the electro-optical array in a fixed position referenced from a fixed reference for measurement purposes; and
   a far-field measurement system for polarization-resolving an optical measurement of the individual chips as a function of the fixed reference.

2. The tester of claim 1 wherein the far-field measurement system comprises:
   a movable measurement system for moving at least one optical characterizer with respect to the fixed reference, in at least one relative direction, with respect to the fixed position of the electro-optical array, the movable measurement system having
   a prober for selectively probing a selected chip of the electro-optical array in the fixed position,
   the at least one optical characterizer having at least one member selected from a group comprising a narrowband wavelength-selective filter and a polarization-selective filter for spatially moving about the selected chip for collecting an emission; and
   a controller for compiling the optical measurement by resolving the emission as a function of the angular position of the at least one optical characterizer to the selected chip.

3. The tester of claim 2 wherein the at least one optical characterizer comprises at least one photodetector.

4. The tester of claim 3 wherein the at least one photodetector comprises:
   at least a first pair of TM photodetectors for collecting a far-field TM emission pattern of the selected chip, wherein one of the pair of TM photodetectors will collect in a far-field horizontal arc path and the one of the pair of TM photodetectors will collect in a far-field vertical arc path;
   at least a second pair of TE photodetectors for collecting a far-field TE emission pattern of the selected chip, wherein one of the pair of TE photodetectors will collect in a far-field horizontal arc path and the one of the pair of TE photodetectors will collect in a far-field vertical arc path;
   a first motor-driven arm for mounting and moving a first one of the TM and TE photodetectors in the far-field horizontal arc path relative to the selected chip to sample the horizontal far-field;
   a second motor-driven arm for mounting and moving a second one of the TM and TE detectors in the far-field vertical arc path relative to the selected chip to sample the vertical far-field; and
   a motion controller for controlling the movement of the at least one of the first and second motor-driven arms to move at least one of the TM and TE pair of photodetectors in the arc path relative to the fixed reference.

5. The tester of claim 4 wherein the chip comprises a semiconductor optical amplifier (SOA) having an amplified spontaneous emission (ASB) wherein the at least first and second pairs of TM and TE photodetectors collect a far-field ASB pattern of the selected SOA.

6. The tester of claim 5 wherein the polarization-selective filter comprises a TE polarizing filter, for selecting the TE polarization vectors to received by the photodetector.

7. The tester of claim 5 wherein the controller determines an integrated total ASE power from the far-field ASE pattern of the selected SOA.

8. The tester of claim 7 wherein the controller determines gain of the SOA from the integrated total ASE power of the selected SOA for both TE and TM polarizations.

9. The tester of claim 8, wherein the controller determines a polarization dependent gain (PDG) as the difference in TE gain and TM gain.

10. The tester of claim 4 wherein the chip comprises a laser wherein the at least first and second pairs of TM and TE photodetectors collect a far-field power measurement of the selected laser.

11. The tester of claim 4 wherein the polarization-selective filter comprises a TM polarizing filter for selecting the TM polarization vectors to be received by the photodetector.

12. The tester of claim 4 wherein the narrowband wavelength-selective filter comprises a narrow bandpass filter for transmitting wavelengths about a selected wavelength $\lambda$ in a narrow bandwidth approximately between $\lambda - \Delta\lambda/2$ to $\lambda + \Delta\lambda/2$.

13. The tester of claim 12 wherein the narrowband wavelength-selective filter comprises a second narrow bandpass filter for transmitting wavelengths in a second bandwidth approximately between $\lambda_2 - \Delta\lambda_2/2$ to $\lambda_2 + \Delta\lambda_2/2$ such that the optical output at different wavelengths can be optically characterized.

14. The tester of claim 4 wherein the movable measurement system comprises a plurality of lock-in amplifiers for synchronizing a corresponding photodetector with the current modulation applied by the controller to a current amplifier for current injection of the selected chip for improving accuracy of the movable measurement system.

15. The tester of claim 14 wherein the controller determines gain of the SOA from the integrated total ASE power of the selected SOA as the injection current level to the selected SOA is varied by the controller to determine gain as a function of current.

16. The tester of claim 2 wherein the at least one optical characterizer comprises an integrating sphere when the chip emits in a small diverging angle.

17. The tester of claim 16, wherein the chip comprises a semiconductor optical amplifier (SOA), wherien the integrating sphere laterally moves towards the selected SOA for collecting an amplified spontaneous emission (ASE).

18. A method for screening individual ones of a semiconductor device of an electro-optical array, the method comprising the steps of:
   providing a fixed reference for measurement purposes;
   securing the electro-optical array in a fixed position referenced from the fixed reference, wherein the securing step comprises the steps of:
   stepping a probe towards the electro-optical array in a first step size;
   checking to determine if an electrical loop is closed on the electro-optical array;
   continuing to step the probe continuously in a second step size that is continuously smaller than the previous step size, as expected contact is approximated, toward the laser array until the electrical loop is closed; and
   contacting the electro-optical array in the fixed position with the probe and securing the probe in a contact position for closing the electrical loop, wherein the contact position is not moved from the fixed reference and contact is maintained as the fixed reference and as the fixed position for all subsequent polarization-resolving of optical measurements of the same individual one of the semiconductor devices of the electro-optical array; and moving at least one detector to a selected position referenced from the fixed reference, wherein the selected position of the at least one detector is also changed from the fixed position of the laser array.

19. The method of claim 18 wherein the moving step comprises the steps of:
vertically moving a prober for selectively probing a selected semiconductor device of the electro-optical array in the fixed position;
moving a first pair of TM and TE detectors in a horizontal arc path relative to the selected semiconductor device to sample a horizontal far-field in a selected narrow wavelength passband; and
moving a second pair of TM and TE detectors in a vertical arc path relative to the selected semiconductor device to sample a vertical far-field in the selected narrow wavelength passband.

20. A tester for screening individual ones of a semiconductor device of an electro-optical array, the tester comprising:
a vacuum suction for securing the array while the array is moved horizontally to a preselected indexed position referenced from a fixed reference;
a vacuum held and temperature controlled semiconductor electro-optical device array array assembly for receiving the vacuum suction and holding the array in the fixed position once the selected semiconductor device has been moved horizontally to the preselected indexed position referenced from the fixed reference;
a vertically movable prober for contacting the selected semiconductor device at the preselected indexed position at a contact position, wherein the contact position is not moved from the fixed reference and contact is maintained as the fixed reference and as the fixed position for all subsequent optical measurements of the same individual one of the semiconductor device of the electro-optical array; wherein the vertically movable prober comprises:
a fixture controllable for providing a vertical movement;
a first probe mounted on the fixture for contacting the selected semiconductor device at the preselected indexed position;
a second probe mounted on the fixture for contacting the vacuum held and temperature controlled laser array assembly for minimizing microwave reflections; and
at least one movable detector movable from the fixed reference for polarization resolving an optical measurement of the selected semiconductor device as a function of the distance moved by the at least one detector with reference to the preselected indexed position of the selected semiconductor device, wherein the change in angular displacement of the at least one detector from the preselected indexed position of the selected semiconductor device is the same change in distance of the at least one detector from the fixed reference.

* * * * *